(12) United States Patent
Kim et al.

(10) Patent No.: US 9,465,003 B2
(45) Date of Patent: Oct. 11, 2016

(54) MEMBRANE PHASE ELECTRODE USING PRINTING AND BIO-MOLECULE DETECTION USING SAME

(75) Inventors: Min Gon Kim, Daejeon (KR); Jun Hyoung Ahn, Daejeon (KR); Yun Ju Sung, Daejeon (KR); Yong Beom Shin, Daejeon (KR); Hyo Arm Joung, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 44 days.

(21) Appl. No.: 13/994,348

(22) PCT Filed: Dec. 16, 2011

(86) PCT No.: PCT/KR2011/009746
§ 371 (c)(1),
(2), (4) Date: Jun. 20, 2013

(87) PCT Pub. No.: WO2012/081940
PCT Pub. Date: Jun. 21, 2012

(65) Prior Publication Data
US 2013/0264221 A1    Oct. 10, 2013

(30) Foreign Application Priority Data

Dec. 16, 2010  (KR) .................. 10-2010-0128965
Dec. 16, 2011  (KR) .................. 10-2011-0136334

(51) Int. Cl.
*G01N 27/327*   (2006.01)
*G01N 33/543*   (2006.01)
(Continued)

(52) U.S. Cl.
CPC ......... *G01N 27/3278* (2013.01); *A61B 5/1486* (2013.01); *G01N 27/3275* (2013.01); *G01N 33/54366* (2013.01); *B82Y 5/00* (2013.01); *B82Y 15/00* (2013.01)

(58) Field of Classification Search
CPC .................. G01N 27/3278; G01N 33/54366
USPC ........... 427/2.11, 2.13; 204/403.11; 977/779, 977/904
See application file for complete search history.

(56) References Cited

U.S. PATENT DOCUMENTS 5,284,571 A *  2/1994  Verbrugge ................. 205/118
6,210,907 B1 *  4/2001  Cha .......................... C12Q 1/005
                                                  204/400

(Continued)

FOREIGN PATENT DOCUMENTS

EP         1043588 A1   10/2000
EP         1939627 A1 *  7/2008  ............... B82Y 5/00
KR    10-2002-0091473 A   12/2002

OTHER PUBLICATIONS

Castaneda et al. Electrochemical Sensing of DNA Using Gold Nanoparticles. Electroanalysis. vol. 19, No. 7-8, pp. 743-753 2007.*

(Continued)

*Primary Examiner* — Cachet Sellman
(74) *Attorney, Agent, or Firm* — Panitch Schwarze Belisario & Nadel LLP (57) ABSTRACT

A membrane electrode includes a novel sensor combining a filtering function of a membrane and a signal measuring ability of an electrode. A target material may be measured by filtration through the membrane. A small amount of target materials may be detected with high sensitivity using an amplified electrical signal by increasing electrical conductivity by reducing metal ions on the membrane, and thus the target material may be subject to quantitative analysis. In addition, only a target material selectively binding to a receptor may be filtrated by passing a sample through the membrane after a receptor material is fixed to the electrode, and thus may be used to detect an electrical signal. In addition, the sensor may measure a signal in various methods such as electrical conductivity, impedance, etc.

6 Claims, 9 Drawing Sheets

(51) Int. Cl.
*A61B 5/1486* (2006.01)
*B82Y 5/00* (2011.01)
*B82Y 15/00* (2011.01)

(56) References Cited

U.S. PATENT DOCUMENTS

| | | | |
|---|---|---|---|
| 6,576,460 B1 | 6/2003 | Baeumner et al. | |
| 2002/0055127 A1* | 5/2002 | Gindilis | 435/7.9 |
| 2004/0026266 A1* | 2/2004 | Atkinson et al. | 205/778 |
| 2004/0152067 A1 | 8/2004 | Wang et al. | |
| 2008/0292545 A1* | 11/2008 | Lin et al. | 424/1.29 |
| 2009/0084686 A1* | 4/2009 | Yun et al. | 205/792 |
| 2010/0194409 A1* | 8/2010 | Gao | C12Q 1/6825 324/693 |

OTHER PUBLICATIONS

Int'l Search Report and Written Opinion issued Jul. 27, 2012 in Int'l Application No. PCT/KR2011/009746.

Dharuman et al, "Label-free impedance detection of oligonucleotide hybridisation on interdigitated ultramicroelectrodes using electrochemical redox probes," Biosensors and Bioelectronics, vol. 21, pp. 645-654 (2005).

Yang et al, "Interdigitated Array Microelectrode-Based Electrochemical Impedance Immunosensor for Detection of *Escheria coli* O157:H7," Analytical Chemistry, vol. 76, No. 4, pp. 1107-1113 (Feb. 15, 2004).

Ninet et al, "Assessment of the Accuprobe Listeria monocytogenes Culture Identification Reagent Kit for Rapid Colony Confirmation and Its Application in Various Enrichment Broths," Applied and Environmental Microbiology, vol. 58, No. 12, pp. 4055-4059 (Dec. 1992).

Hermans, "CO, CO2, CH4 and H2O Sensing by Polymer Covered Interdigitated Electrode Structures," Sensors and Actuators, vol. 5, pp. 181-186 (1984).

\* cited by examiner

MEMBRANE PHASE ELECTRODE USING PRINTING AND BIO-MOLECULE DETECTION USING SAME

CROSS-REFERENCE TO RELATED APPLICATION

This application is a Section 371 of International Application No. PCT/KR2011/009746, filed Dec. 16, 2011, which was published in the Korean language on Jun. 21, 2012, under International Publication No. WO 2012/081940 A2. This application also claims priority to and the benefit of Korean Patent Application Nos. 10-2010-0128965 and 10-2011-0136334, filed Dec. 16, 2010 and Dec. 16, 2011, respectively, the disclosures of which are incorporated herein by reference.

BACKGROUND

1. Field of the Invention

The present invention relates to a method of detecting a biomaterial using a combination of a filtering characteristic of a membrane and signal measurement of an electrode by forming the electrode on the filtering membrane by screen printing.

2. Discussion of Related Art

Quantitative analysis of a biomaterial is an important technique used in foods, medicine and diagnosis. In particular, rapid detection of microorganisms is a very important technique in diagnosis of food poisoning bacteria, detection of environmentally harmful bacteria and infections, and diagnosis of pathogenic viruses. As a generally and widely used method of examining for the presence and concentration of pathogenic materials (microorganisms, proteins, etc.), a colony method, a DNA probe method, and an immunoassay method are widely used (Jay J M. Modern Food Microbiology, 1986, 3rd, ed., p 95, Van Nostrand Reinhold Co., New York; Tenover F C., DNA Probes for Infectious Diseases, 1989, p 53 CRC Press, Boca Raton). The colony method is a method of counting the number of colonies formed by microorganisms cultured in a selective medium having ingredients allowing only microorganisms from a sample to survive and be detected. This is a very accurate but time-consuming method, and there is difficulty in selecting a medium with respect to a microorganism. The DNA probe method is a method including a real time polymerase chain reaction (PCR) and nucleic acid hybridization, and is used to detect DNA in a cell by nucleic acid conjugation after microorganisms are disrupted by a physicochemical method. This is faster than the colony method in detecting microorganisms. However, it needs expensive PCR equipment and requires separate incubation to obtain high sensitivity when a small amount of microorganisms is detected (Ninet, B et al., Appl Environ Microbiol 58:4055-4059, 1992). If incubation is not included, dead cells may be detected, which leads to inaccurate results. In addition, when PCR is performed, a range of detection errors becomes wide due to frequent false-positive results, and thus it is possible to decrease reliability of the analysis. The immunoassay method uses an antigen-antibody binding reaction. An enzyme-linked immunosorbent assay (ELISA) using an antibody specifically reacting with a surface antigen of a microorganism to be detected is widely used. This is considered as an alternative to the above-described two methods since it achieves very high sensitivity in a short time.

The present invention is directed to providing a sensor that combines a measurement capability of an electrode and a filtering characteristic of a membrane, by forming the electrode on the filtering membrane.

SUMMARY OF THE INVENTION

The present invention is directed to providing a sensor for detecting a biomaterial by combining a measurement capability of a sensor of an electrode and a separation ability of a filtering membrane, by forming an electrode on the filtering membrane, a method of manufacturing the same, and a method of detecting a target material using the same.

One aspect of the present invention provides a sensor having an electrode printed on a filtering membrane. A reaction solution prepared by mixing a ligand-fixed enzyme or ligand-fixed metal nanoparticles and a sample containing a target material passes through the filtering membrane, thereby generating an electrical signal in the electrode.

Another aspect of the present invention provides a method of manufacturing a sensor, which includes: (a) printing an electrode on a filtering membrane; and (b) passing a reaction solution prepared by mixing a ligand-fixed enzyme or ligand-fixed metal nanoparticles and a sample containing a target material through the filtering membrane.

Still another aspect of the present invention provides a method of detecting a target material, which includes: (a) mixing a ligand-fixed enzyme or ligand-fixed metal nanoparticles and a sample containing a target material to react; (b) filtering only a target material-ligand-enzyme complex or target material-ligand-metal nanoparticle complex by passing the reaction solution through a filtering membrane having an electrode; and (c) measuring an electrical signal generated in the electrode by a target material-ligand-enzyme complex or target material-ligand-metal nanoparticle complex remaining on the filtering membrane.

Yet another aspect of the present invention provides a method of detecting a target material, which includes: (a) mixing a ligand-fixed enzyme or ligand-fixed metal nanoparticles and a sample containing a target material to react; (b) filtering only a target material-ligand-enzyme complex or target material-ligand-metal nanoparticle complex specifically binding to a receptor by passing the reaction solution through a filtering membrane between electrodes; and (c) measuring an electrical signal generated in the electrodes by a target material-ligand-enzyme complex or target material-ligand-metal nanoparticle complex remaining on the filtering membrane.

BRIEF DESCRIPTION OF THE DRAWINGS

The above and other objects, features, and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail. However, the present invention is not limited to the exemplary embodiments disclosed below, but can be implemented in various forms. The following embodiments are described in order to enable those of ordinary skill in the related art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements.

The terminology used herein is for the purpose of describing particular embodiments only and is not intended to be limiting of exemplary embodiments. The singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

The present invention provides a sensor having an electrode printed on a filtering membrane. Here, a reaction solution prepared by mixing a ligand-fixed enzyme or ligand-fixed metal nanoparticles and a sample containing a target material passes through the filtering membrane, thereby generating an electrical signal in the electrode.

Specifically, the sensor has electrodes printed on a filtering membrane. When a reaction solution prepared by mixing a ligand-fixed enzyme or ligand-fixed metal nanoparticles and a sample containing a target material passes through the filtering membrane, a reaction solution not bound with the target material may pass through the membrane and thus only a target material-ligand-enzyme complex or target material-ligand-metal nanoparticle complex bound with the target material may remain, thereby generating an electrical signal in the electrodes.

In the present invention, the "filtering membrane" refers to a filter having small pores having a diameter of 100 nm to 10 μm. Accordingly, when a reaction solution prepared by reacting a mixture of a ligand-fixed enzyme or ligand-fixed metal nanoparticles and a sample containing a target material passes through the filtering membrane, a filtering function in which a ligand-fixed enzyme or ligand-fixed metal nanoparticles that are not bound with a target material may pass through the membrane, and thus only a target material-ligand-enzyme complex or target material-ligand-metal nanoparticle complex bound with the target material may remain on the membrane, thereby generating a signal by the electrodes formed on the membrane may be performed.

The filtering membrane may be, for example, a nitrocellulose, polycarbonate, nylon, polyester, cellulose acetate, polysulfone or polyethanesulfone filter, but the present invention is not limited thereto.

According to an exemplary embodiment of the present invention, the electrode may be printed by screen printing, specifically, a silk screen printing process. For example, the electrode may be formed by directly printing a paste of an electrode material (platinum, gold, silver, carbon, etc.) on a membrane through a screen having a predetermined pattern, and drying the printed result at high temperature (generally, 100° C. or more). This process may be repeatedly performed.

The electrode may be, for example, an interdigitated electrode (IDE). In the IDE, two comb-shaped electrodes face each other. The IDE is used to detect food poisoning bacteria since a microorganism can be detected by an impedance method when microorganisms are bound between insulation of the two electrodes (Yang, L. et al. Anal. Chem., 76:1107-1113, 2004). In addition, the IDE is used as various sensors such as a non-labeled biosensor, a gas sensor, etc. (Dharuman, V. et al. Biosens. Bioelectron., 21:645-654, 2005, Hermans E. C. M., Sensor. Actuat. 5:181-186, 1984).

The interdigitated electrode may have a gap between electrodes of, for example, 10 to 1000, 10 to 900, 10 to 800, 10 to 700, 10 to 600, 10 to 500, 10 to 450, 10 to 400, 10 to 350, 1 to 300, 10 to 250, 10 to 200 or 10 to 150 μm, but the present invention is not limited thereto.

In the present invention, the "ligand" is a material having specific binding affinity for a target material, which may be, for example, an antibody, an antigen, an enzyme, a peptide, a protein, DNA, RNA, peptide nucleic acid (PNA) or an aptamer, but the present invention is not limited thereto. The kind of the ligand may be suitably selected by one of ordinary skill in the art according to the kind of the target material to be detected.

When the ligand-fixed enzyme or ligand-fixed metal nanoparticles are mixed with the sample containing the target material to react, a "target material-ligand-enzyme complex" or "target material-ligand-metal nanoparticle complex", in which a target material and an enzyme, or a target material and metal nanoparticles, are bound with each other by the ligand in the mixed reaction solution, may be prepared. Here, a ligand-fixed enzyme or ligand-fixed metal nanoparticles that are not bound with the target material pass through the membrane, and only the target material-ligand-enzyme complex or target material-ligand-metal nanoparticle complex that is bound with the target material remains on the membrane, thereby generating an electrical signal in the electrode formed on the membrane. By measuring the electrical signal, the target material may be detected. Particularly, since the measured electrical signal is proportional to a concentration of the metal nanoparticles remaining on the membrane (that is, a concentration of the target material), the target material can be quantitatively detected.

Particularly, when the target material is a microorganism, a cell or an organ of an animal or plant, which has a large size, the target material may be easily detected without a separate receptor equipped on the membrane. In the present invention, the "target material" may be a microorganism, an antigen, a nucleic acid, a cell or an organ of an animal or plant, and here, the "microorganism" may be, but is not limited to, for example, a virus, a bacterium or a fungus.

In the present invention, the ligand-fixed "enzyme" may be, but is not limited to, for example, a peroxidase, an alkaline phosphatase, a galactosidase, or a glucose oxidase, and the ligand-fixed "nanoparticle" may be, but is not limited to, for example, gold, silver, copper or a magnetic nanoparticle.

In the present invention, the "nanoparticle" refers to a superfine particle having a diameter of approximately 1 to 100 nm. In one embodiment of the present invention, nanoparticles having a size of 20 nm are used, but the present invention is not limited thereto. Nanoparticles may have a size of 0.5 to 100, 0.5 to 90, 0.5 to 80, 0.5 to 70, 0.5 to 60, 0.5 to 50, 0.5 to 40, 0.5 to 30, 0.5 to 20 or 1 to 20 nm.

According to another embodiment of the present invention, a sensor including a receptor additionally fixed on a filtering membrane between electrodes may be manufactured.

According to the exemplary embodiment, the sensor of the present invention includes the receptor additionally fixed on the filtering membrane between electrodes, and thus only a target material-ligand-enzyme complex or target material-ligand-metal nanoparticle complex specifically binding to the receptor remains on the membrane, thereby generating an electrical signal in the electrode.

The "receptor" is a material having specific affinity for the target material, and has a binding site different from the ligand binding a target material with an enzyme or ligand-fixed metal nanoparticles. After electrodes are formed on the membrane, the receptor may be fixed on the membrane between the electrodes. The receptor may be fixed by a method known in the art, and any one of physical adsorbing methods and chemical methods may be used. A specific fixing method may be suitably selected by one of ordinary skill in the art according to the kinds of the receptor and membrane.

When a reaction solution prepared by mixing a ligand-fixed enzyme or ligand-fixed metal nanoparticles and a sample containing a target material is added to the sensor having the additionally fixed receptor, the target material specific to the receptor is bound with the receptor on the membrane, thereby forming a receptor-target material-ligand-enzyme complex or receptor-target material-ligand-metal nanoparticle complex. Accordingly, the complex is fixed on the membrane, and the target material specific to the receptor may be detected by an electrical signal.

The receptor may be, but is not limited to, for example, an antibody, an antigen, an enzyme, a peptide, a protein, DNA, RNA, PNA, or an aptamer.

The target material may be, but is not limited to, for example, an antibody, an antigen, an enzyme, a peptide, a protein, DNA, RNA, a microorganism, a cell or an organ of an animal or plant.

According to still another embodiment of the present invention, a sensor without a receptor or having an additionally fixed receptor, in which metal ions are reduced and precipitated on a surface of an electrode by adding a metal reducing solution on a filtering membrane, may be manufactured.

According to the exemplary embodiment, the sensor of the present invention may have an electrode printed on the filtering membrane, and metal ions may be reduced and precipitated on a surface of the electrode.

According to an exemplary embodiment of the present invention, as described above, the metal ions are reduced by the metal reducing solution to be precipitated on a surface of the electrode, but the present invention is not limited thereto. Metal ions may be reduced and precipitated on a surface of the electrode by a method that is suitably selected by one of ordinary skill in the art. An electrical signal generated by a target material-ligand-enzyme complex, a material-ligand-metal nanoparticle complex, a receptor-target material-ligand-enzyme complex or a receptor-target material-ligand-metal nanoparticle complex remaining on the membrane may be amplified by increased electrical conductivity due to the addition of a metal reducing solution to reduce and precipitate metal ions on a surface of the electrode.

Here, the "metal reducing solution" refers to a solution including metal ions and a reducing agent capable of reducing the metal ions. Any solution having such a characteristic may be used without limitation, and a specific composition may be suitably selected by one of ordinary skill in the art.

Here, the metal ions may be, but are not limited to, at least one selected from the group consisting of gold, silver and copper. In addition, a reducing agent capable of reducing the metal ions may be selected from, for example, hydroxylamine ($NH_2OH$), ascorbic acid, glucose and a mixture thereof, but the present invention is not limited thereto.

As the metal ions are reduced by the metal reducing solution, and precipitated on a surface of the electrode on the membrane, electrical conductivity of the electrode is increased, resulting in amplification of an electrical signal. Here, the reduction of such metal ions may be considerably stimulated by the ligand-fixed enzyme or ligand-fixed metal nanoparticles added to the membrane, and the electrical conductivity may be considerably enhanced due to the enzyme or ligand-fixed metal nanoparticles, thereby manufacturing a sensor having excellent detection sensitivity.

Figure 3:
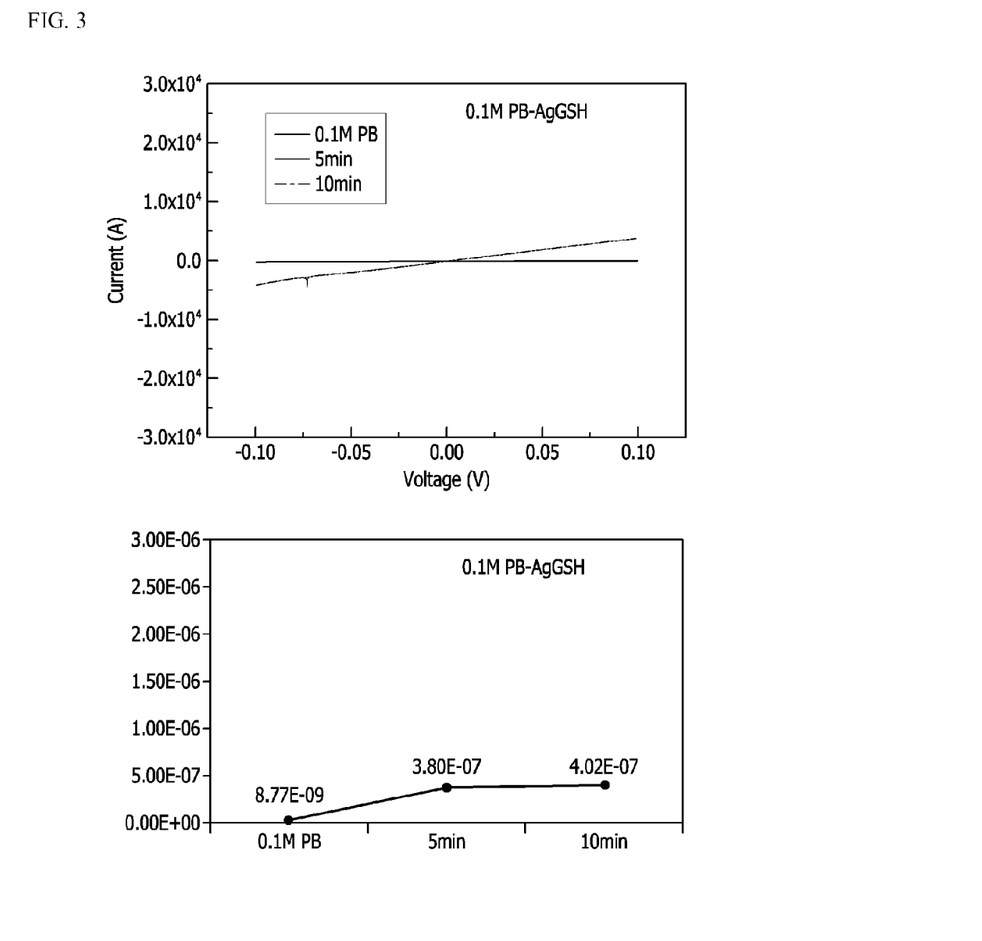
FIGS. 3 and 4 are graphs showing a change in current according to the presence of an enzyme and silver ion reduction on a membrane silver electrode according to the present invention (0.1M PB—AgGSH: control group without enzyme; STA/HRP—AgGSH: test group having enzyme)
Figure 4:
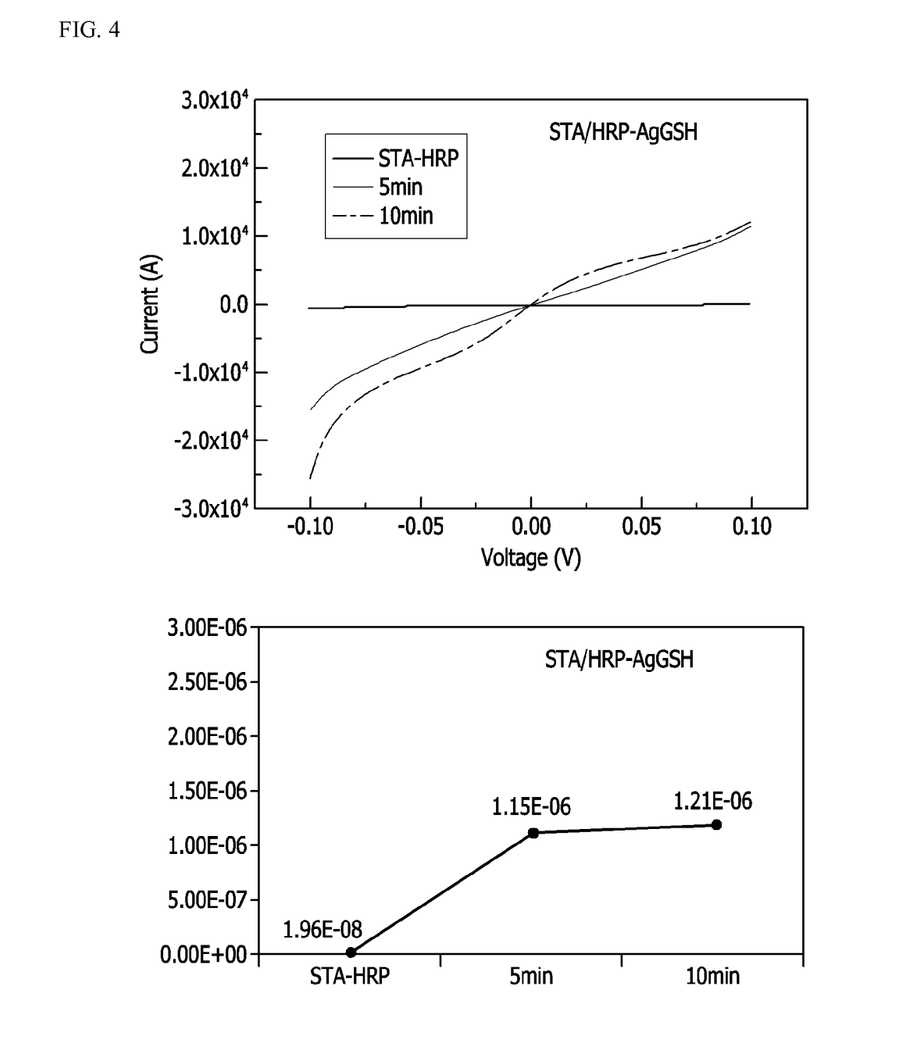

According to the following embodiment, it can be noted that the electrical conductivity may be considerably enhanced since a reduction rate of silver ions in a silver reducing solution is higher in the case (STA/HRP—AgGSH) that the silver ions are reduced by adding the silver reducing solution in the presence of a peroxidase enzyme, compared with a control group (PB—AgGSH) in which silver ions are reduced by adding only a silver reducing solution to an electrode (refer to FIGS. 3 and 4).

Figure 6:
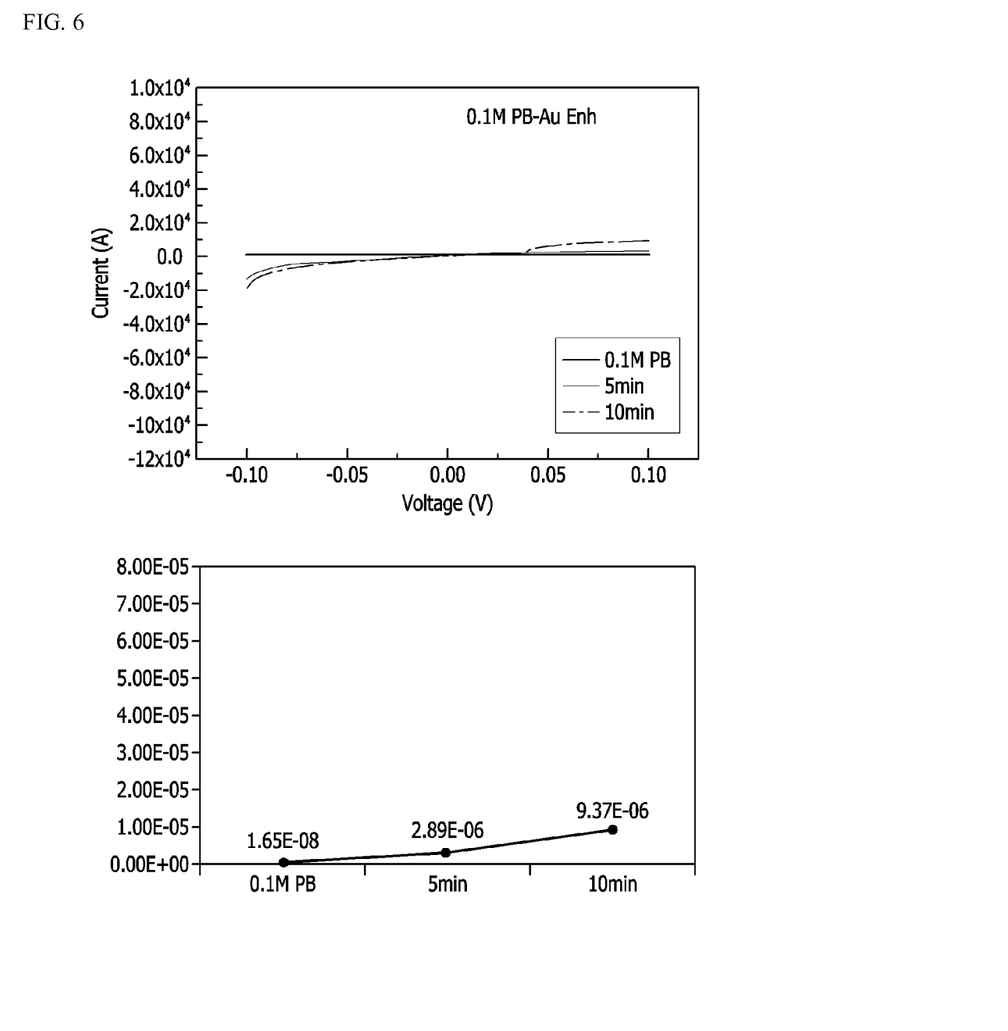
FIGS. 6 and 7 are graphs showing a change in current according to the presence of gold nanoparticles and gold ion reduction on a silver micro-electrode according to the present invention (0.1M PB—Au Enh: control group without gold nanoparticles; AuNP—Au Enh: test group having gold nanoparticles)
Figure 7:
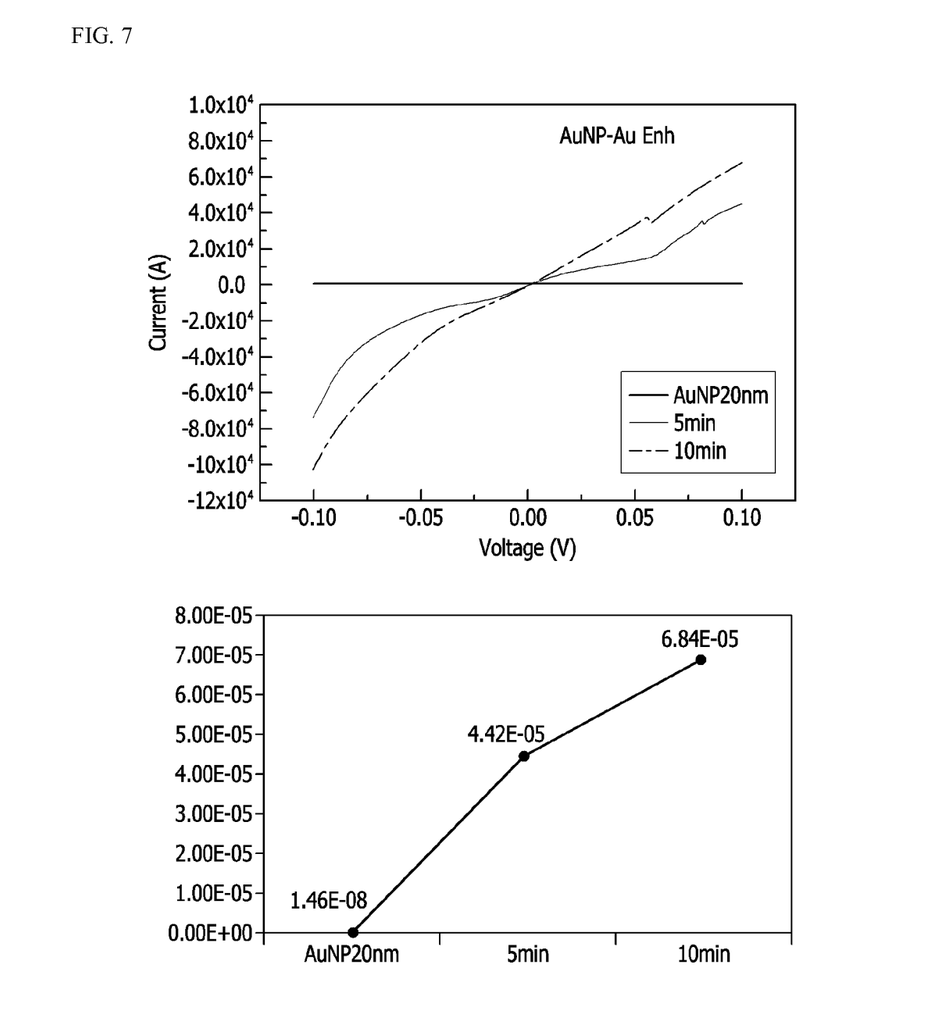

According to yet another embodiment, it can be noted that electrical conductivity is considerably enhanced since a reduction rate of gold ions in a gold reducing solution is higher in the case (AuNP—Au Enh) that the gold ions are reduced by treating the gold reducing solution in the presence of gold nanoparticles, compared with a control group (PB—Au Enh) in which an electrode is treated with only a gold reducing solution (refer to FIGS. 6 and 7).

In addition, the present invention provides a method of manufacturing a sensor, which includes: (a) printing an electrode on a filtering membrane; and (b) passing a reaction solution prepared by mixing a ligand-fixed enzyme or ligand-fixed metal nanoparticles and a sample containing a target material through the filtering membrane.

After operation (a), the method may further include additionally fixing a receptor on the filtering membrane between electrodes.

According to an exemplary embodiment of the present invention, the method may further include reducing and adding metal ions on a surface of the electrode by adding a metal reducing solution on the filtering membrane of the sensor that does not have the receptor, or has the additionally-fixed receptor.

In the method of manufacturing a sensor of the present invention, the electrode, the ligand, the enzyme, the nanoparticles, the target material, the receptor, the metal reducing solution, etc. may be the same as in the sensor described above.

In addition, the present invention provides a method of detecting a target material, which includes: (a) reacting a mixture of a ligand-fixed enzyme or ligand-fixed metal nanoparticles and a sample containing a target material; (b) passing the reaction solution through the filtering membrane having an electrode to filter only a target material-ligand-enzyme complex or target material-ligand-metal nanoparticle complex; and (c) measuring an electrical signal generated in the electrode by a target material-ligand-enzyme complex or target material-ligand-metal nanoparticle complex remaining on the filtering membrane.

In addition, the present invention provides a method of detecting a target material, which includes: (a) reacting a mixture of a ligand-fixed enzyme or ligand-fixed metal nanoparticles and a sample containing a target material; (b) passing the reaction solution through the filtering membrane having a receptor fixed on a filtering membrane between electrodes to filtrate only a target material-ligand-enzyme complex or target material-ligand-metal nanoparticle complex specifically binding to the receptor; and (c) measuring an electrical signal generated in the electrodes by a target material-ligand-enzyme complex or target material-ligand-metal nanoparticle complex remaining on the filtering membrane.

Before measurement of the electrical signal, the method may further include reducing and depositing metal ions on a surface of the electrodes by adding a metal reducing solution on the filtering membrane.

The electrical signal may be amplified into a signal capable of being electrically measured by means of the enzyme or metal, and then measured.

In an embodiment of the present invention, the measured signal may be an electrical signal measured by an electrode on the membrane, and for example, by measurement of electrical conductivity or impedance, but the present invention is not limited thereto.

The method of detecting a target material of the present invention may be performed using the above-described sensor, and thus may include all the configuration and characteristics of the above-described sensor.

The present invention will now be described in further detail with reference to Examples. The following Examples are provided to fully describe the present invention, and should not be construed as limiting its scope.

EXAMPLES

Example 1

Silver Ion Reduction after Enzyme is Fixed to Membrane Silver Electrode

Electrodes interdigitated with a gap of 100 μm were formed using a silver paste on an asymmetric super-micron membrane (MMM) having a pore size of 0.45 μm through a silk screen printing technique.

A peroxidase enzyme was fixed between the interdigitated electrodes, and reacted with 0.1 M citrate buffer (pH 8.5, silver reducing solution) containing 1 mM silver acetate, 1 mM glutathione, 10 mM hydroquinone and 100 mM hydrogen peroxide to reduce silver ions between the electrodes. Here, a direct current voltage was applied, and a current was measured.

Figure 1:
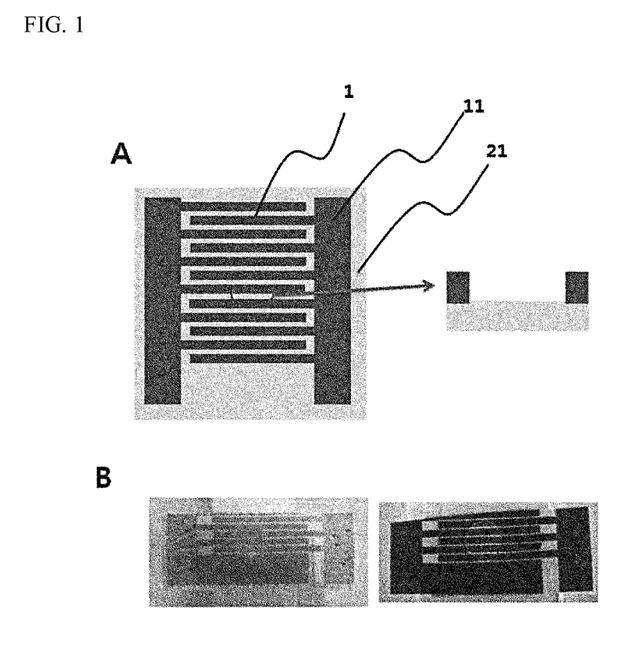
FIG. 1 shows a diagram of membrane electrodes formed with a gap of 100 μm using a silk screening printing process (A), and images of a membrane silver electrode (B, left) and a membrane carbon electrode (B, right)
Figure 2:
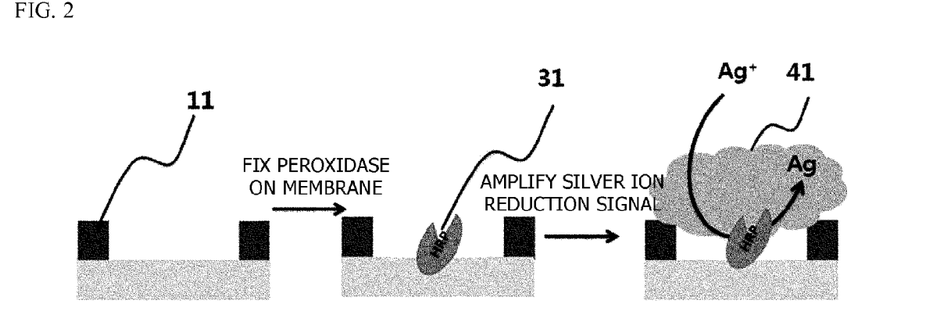
FIG. 2 is a diagram showing a process of forming a silver ion reduction precipitate using an enzyme on a membrane silver electrode according to the present invention.

FIG. 2 is a diagram showing a process of fixing a peroxidase enzyme (HRP) to the membrane silver electrode formed as described above, and reducing silver ions in the silver reducing solution prepared as described above on the electrodes by the peroxidase enzyme.

FIGS. 3 and 4 show changes in current measured by fixing a peroxidase enzyme to the membrane silver electrodes formed as described above, reducing silver using the enzyme and the silver reducing solution prepared as described above, and applying a direct current voltage thereto. It could be confirmed that electrical conductivity was considerably enhanced as silver ions were reduced (5 min, 10 min) by treating a silver reducing solution in the test group (STA/HRP—AgGSH) using a peroxidase enzyme, compared with the control group (PB—AgGSH) without a peroxidase enzyme.

Example 2

Gold Ion Reduction after Gold Nanoparticles Were Fixed to Membrane Silver Electrode Electrodes interdigitated with a gap of 100 μm were formed using a silver paste on an asymmetric super-micron membrane (MMM) having a pore size of 0.45 μm through a silk screen printing technique.

Gold nanoparticles having a size of 20 nm were fixed between the interdigitated electrodes, and reacted with 10 mM citrate buffer (gold reducing solution, pH 3.0) containing 1 mM hydroxylamine and 10 mM $HAuCl_4$ to reduce gold ions between the electrodes. Here, a direct current voltage was applied, and a current was measured.

Figure 5:
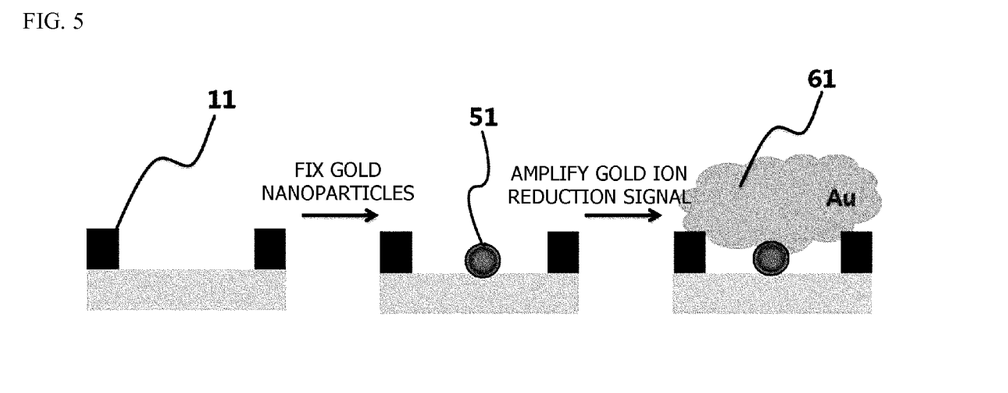
FIG. 5 is a diagram showing a process of forming a gold ion reduction precipitate using gold nanoparticles on a membrane silver electrode according to the present invention.

FIG. 5 is a diagram showing a process of fixing gold nanoparticles to the membrane silver electrode formed as described above, and reducing the gold reducing solution prepared as described above on the electrodes by the gold nanoparticles.

FIGS. 6 and 7 show changes in current measured by fixing gold nanoparticles to the membrane silver micro-electrode formed as described above, reducing gold using the gold reducing solution prepared as described above, and applying a direct current voltage thereto. It could be confirmed that electrical conductivity was considerably enhanced as gold ions were reduced (5 min, 10 min) by treating a gold reducing solution in the test group (AuNP—Au Enh) to which gold nanoparticles were fixed, compared with the control group (PB—Au Enh) without using gold nanoparticles.

Example 3

Gold Ion Reduction after Food Poisoning Bacteria-antibody-gold Nanoparticle Complex was Filtrated Through Membrane Silver Electrode Example 3-1

Preparation of Gold Nanoparticle-antibody Conjugate 0.1 mL of borate buffer (0.1 M, pH 8.5) and 10 μg of an antibody (Abcam, ab20002) having selectivity to *Staphylococcus aureus* were added to 1 mL of a 20-nm gold nanoparticle solution (BB International). After 30 minutes, 0.1 mL of a 1% bovine serum albumin (BSA) solution (pH 8.5, dissolved in 10 mM carbonate buffer) was added to the mixture, and stayed for 30 minutes. The solution was subjected to centrifugation at 4° C. and 10,000 rpm for 20 minutes, and a surfactant was removed. After 1 mL of 0.1% BSA (pH 8.5, dissolved in 10 mM carbonate buffer) was added to and mixed with the mixture, the resulting mixture was subjected to centrifugation at 10,000 rpm for 20 minutes, and then a surfactant was removed. The above process was repeated again, and 0.5 ml of a 0.1% BSA solution (dissolved in PBS buffer) was finally added to and mixed with the resulting mixture, and then stored in a refrigerator.

Example 3-2

Culture of *Staphylococcus aureus*

A stock of *Staphylococcus aureus*, which are food poisoning bacteria, was inoculated into nutrient broth (NB), and incubated at 37° C. in a shaking incubator for 18 to 24 hours. To count colony forming units (CFU) of the incubated bacteria, the culture solution was diluted in a range of $10^5$ to $10^9$, inoculated by 100 μl and plated on a solid plate to be incubated at 37° C. for 16 to 24 hours. Afterward, colonies formed on the plate were counted and multiplied by a dilution rate, thereby measuring a vial cell count. In addition, a suitable amount of a liquid medium containing the incubated bacteria was taken to measure absorbance at a wavelength of 600 nm using a spectrophotometer.

Example 3-3

Analysis of *Staphylococcus aureus*

Electrodes interdigitated with a gap of 100 μm were formed using a silver paste on a polysulfone membrane (Pall life science) having a pore size of 0.45 μm through a silk screen printing technique.

A *Staphylococcus aureus*-antibody-god nanoparticle complex was prepared by reacting *Staphylococcus aureus* with a gold nanoparticle-antibody conjugate for 30 minutes, and filtrated through the membrane silver micro-electrode formed as described above. Here, gold ions were reduced between electrodes by reacting 10 mM citrate buffer (pH 3.0, gold reducing solution) containing 1 mM hydroxylamine and 10 mM $HAuCl_4$ with the filtrated result. Here, a direct current voltage was applied to measure a current.

Figure 8:
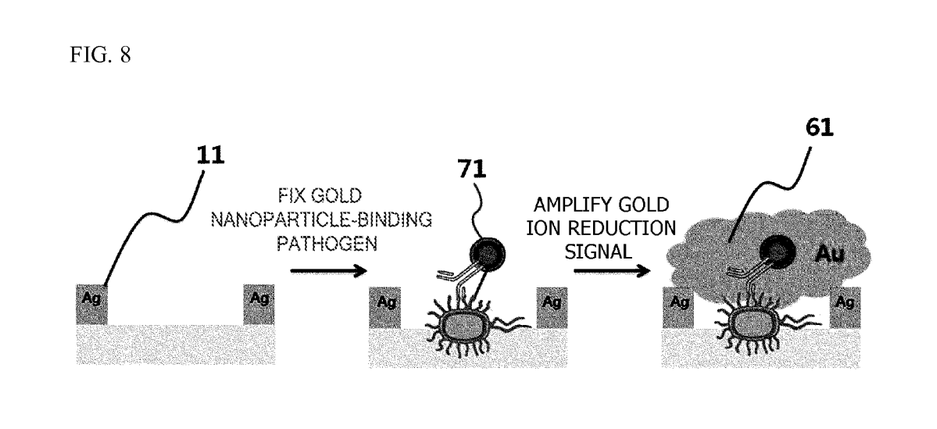
FIG. 8 is a diagram showing a process of forming a gold ion reduction precipitate using a food poisoning bacteria-antibody-gold nanoparticle complex on a membrane silver electrode according to the present invention.

FIG. 8 is a diagram showing fixing a food poisoning bacteria-gold nanoparticle complex to the membrane silver micro-electrode formed as described above, and reducing the gold reducing solution prepared as described above on the electrode by the gold nanoparticles.

Figure 9:
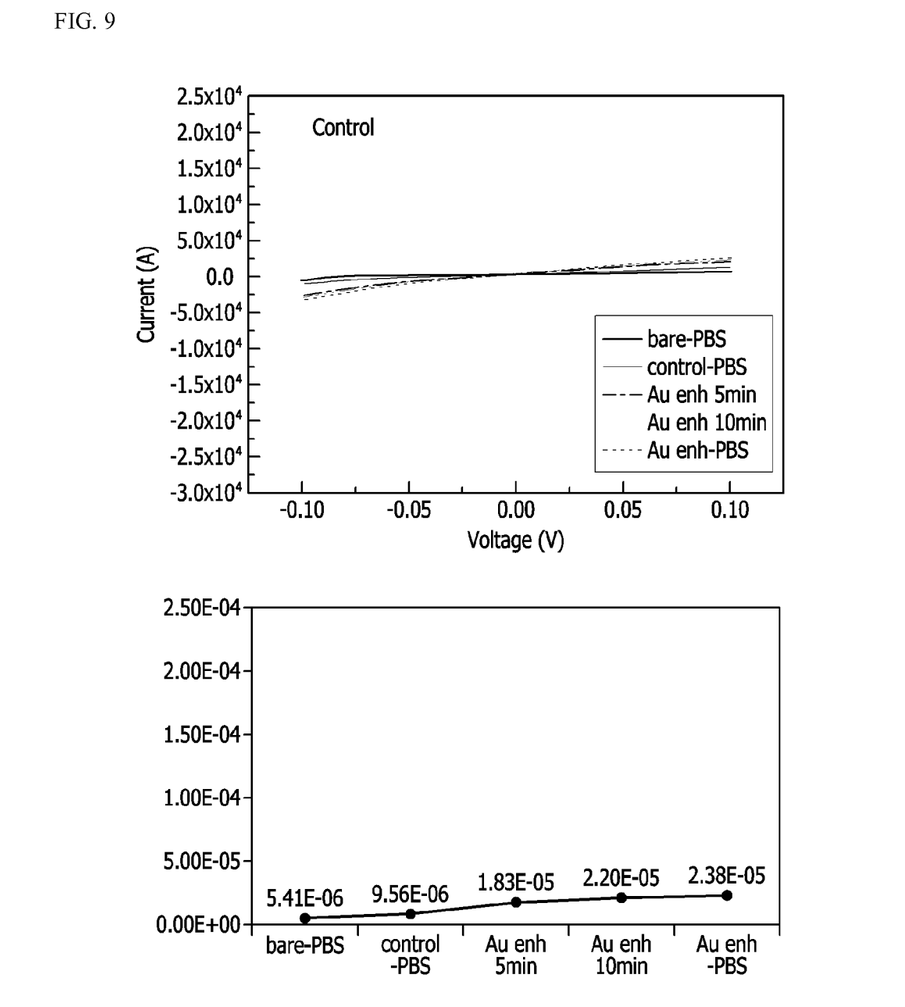
FIGS. 9 and 10 are graphs showing a change in current according to the presence of a food poisoning bacteria-antibody-gold nanoparticle complex and reduction of a gold ion reduction on a membrane silver electrode according to the present invention (Control: control group only having antibody-gold nanoparticle conjugate; $10^2$ cell: test group having complex; bare-PBS: addition of PBS to initial electrode; control-PBS: addition of PBS after gold nanoparticles are added; cell-PBS: addition of PBS after food poisoning bacteria-antibody-gold nanoparticle complex is added; Au enh-5 min: treatment with gold reducing solution for 5 minutes; Au enh 10 min: treatment with gold reducing solution for 10 minutes; Au enh-PBS: washing with PBS after gold reducing solution is treated)
Figure 10:
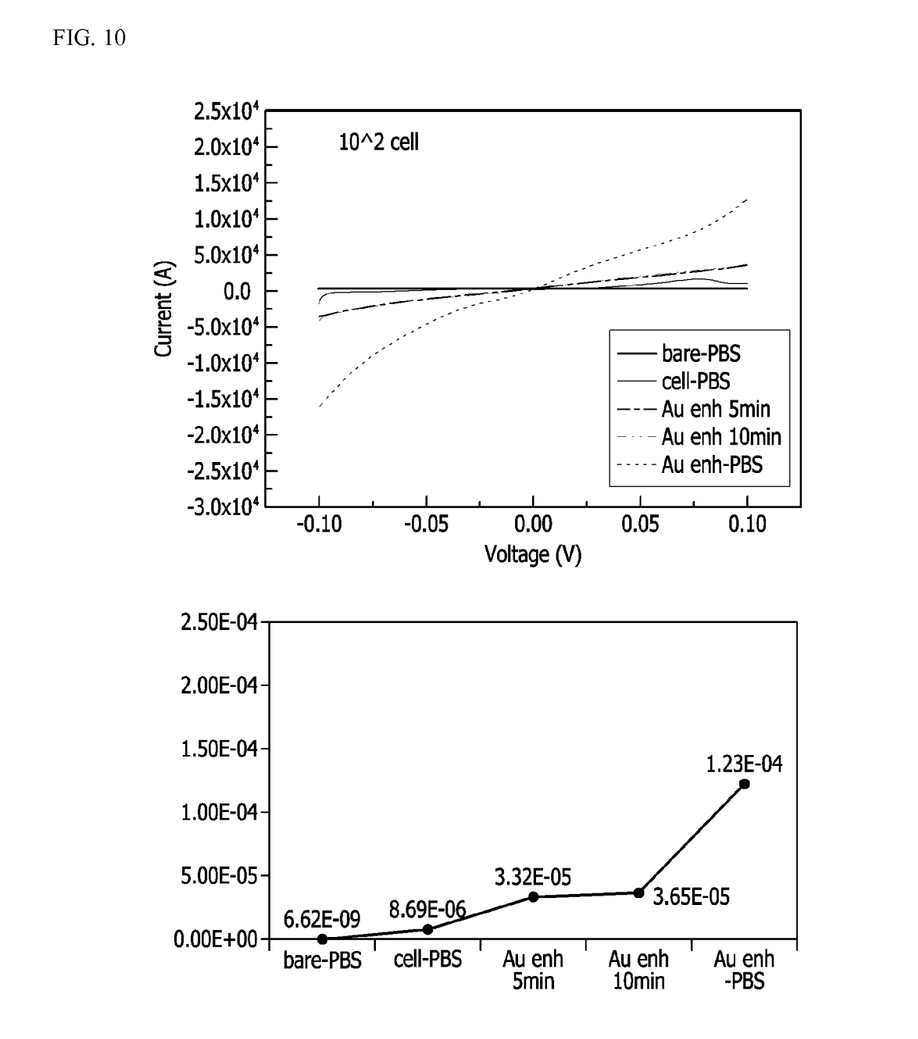

FIGS. 9 and 10 show changes in current measured by fixing a food poisoning bacteria-gold nanoparticle complex to the membrane silver micro-electrode formed as described above, reducing gold using the gold reducing solution prepared as described above, and applying a direct current voltage.

Figure 11:
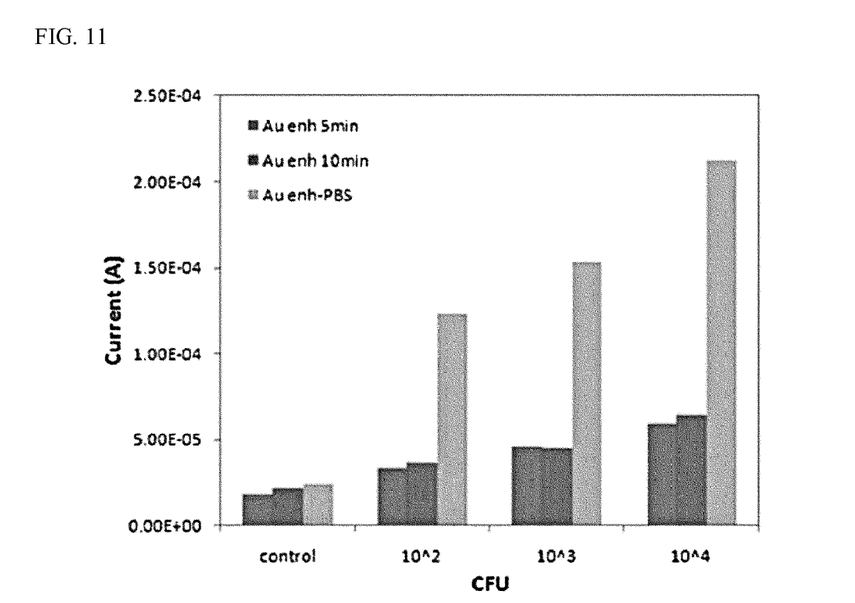
FIG. 11 is a graph showing a change in concentration according to a concentration of *Staphylococcus aureus* on a membrane silver electrode according to the present invention (Au enh-5 min: treatment with gold reducing solution for 5 minutes; Au enh 10 min: treatment with gold reducing solution for 10 minutes; Au enh-PBS: washing with PBS after gold reducing solution is treated).

FIG. 11 shows current values at 0.1 V according to concentrations of *Staphylococcus aureus* from the experiments shown in FIGS. 9 and 10. It is seen that a current value is increased according to the concentration of the bacteria, and may be measured even at a cell concentration of approximately $10^2$ cfu.

The present invention is a result of the research conducted as a part of New Technology-Fused Growth Engine Industry by support from the National Research Foundation of Korea, which was funded by the Government (Ministry of Education and Science Technology (MEST)) in 2011 (2011K000910).

A membrane electrode according to the present invention provides a novel sensor combining a filtering function of a membrane and a signal measuring ability of an electrode. According to the present invention, a target material can be measured by filtration through the membrane, a small amount of target materials can be detected with high sensitivity using an amplified electrical signal by increasing electrical conductivity by reducing metal ions on the membrane, and thus the target material can be subject to quantitative analysis. In addition, only a target material selectively binding to a receptor can be filtrated by passing a sample through the membrane after a receptor material is fixed to the electrode, and thus can be used to detect an electrical signal. In addition, the sensor according to the present invention can measure a signal by various methods such as electrical conductivity, impedance, etc.

While the invention has been shown and described with reference to certain exemplary embodiments thereof, it will be understood by those skilled in the related art that various changes in form and details may be made therein without departing from the scope of the invention as defined by the appended claims.

What is claimed is:
1. A method of manufacturing a sensor, comprising:
   (a) printing electrodes on a filtering membrane;
   (b) passing a reaction solution prepared by mixing ligand-fixed metal nanoparticles and a sample containing a target material through the filtering membrane, wherein only the ligand-fixed metal nanoparticles bound with the target material remain on the filtering membrane; and (c) reducing and adding metal ions on a surface of the electrodes by adding a metal reducing solution on the filtering membrane, wherein the target material is selected from the group consisting of a microorganism, an organ of an animal, and an organ of a plant.

2. The method according to claim 1, wherein the filtering membrane is a filter selected from the group consisting of nitrocellulose, polycarbonate, nylon, polyester, cellulose acetate, polysulfone, and polyethanesulfone.

3. The method according to claim 1, wherein the electrodes are printed by a screen printing process.

4. The method according to claim 1, wherein the electrodes are interdigitated electrodes having a gap of 10 to 1000 μm.

5. The method according to claim 1, wherein the ligand is an antibody, an antigen, an enzyme, a peptide, or a protein.

6. The method according to claim 1, wherein the nanoparticle is a gold, silver, copper or magnetic nanoparticle.

* * * * *